(12) United States Patent
Roszell

(10) Patent No.: US 11,324,848 B2
(45) Date of Patent: May 10, 2022

(54) SYSTEMS AND METHODS FOR DIFFUSING ESSENTIAL OILS

(71) Applicant: Cortney Jo Roszell, Raymond (CA)

(72) Inventor: Cortney Jo Roszell, Raymond (CA)

( * ) Notice: Subject to any disclaimer, the term of this patent is extended or adjusted under 35 U.S.C. 154(b) by 153 days.

(21) Appl. No.: 16/178,456

(22) Filed: Nov. 1, 2018

(65) Prior Publication Data

US 2019/0125915 A1      May 2, 2019

Related U.S. Application Data

(60) Provisional application No. 62/580,448, filed on Nov. 2, 2017.

(51) Int. Cl.
| | |
|---|---|
| *A61L 9/12* | (2006.01) |
| *A63H 3/02* | (2006.01) |
| *A45D 34/00* | (2006.01) |
| *A61L 9/013* | (2006.01) |
| *A61L 9/04* | (2006.01) |
| *A61L 9/014* | (2006.01) |

(Continued)

(52) U.S. Cl.
CPC ............... *A61L 9/12* (2013.01); *A45D 34/00* (2013.01); *A45D 34/02* (2013.01); *A61L 9/013* (2013.01); *A61L 9/014* (2013.01); *A61L 9/042* (2013.01); *A63H 3/02* (2013.01); *A45D 2034/007* (2013.01); *A61L 2209/13* (2013.01); *A63H 3/003* (2013.01)

(58) Field of Classification Search
CPC . A61L 9/12; A61L 9/013; A61L 9/014; A61L 9/042; A61L 2209/13; A45D 34/00; A45D 34/02; A45D 2034/007; A63H 3/02; A63H 3/003

USPC .............................................. 239/34
See application file for complete search history.

(56) References Cited

U.S. PATENT DOCUMENTS

| | | | | |
|---|---|---|---|---|
| 4,020,156 A | * | 4/1977 | Murray ................ | A61K 8/0241 |
| | | | | 424/76.6 |
| 5,037,343 A | * | 8/1991 | Benites .................. | A63H 3/003 |
| | | | | 446/268 |

(Continued)

FOREIGN PATENT DOCUMENTS

| | | | | |
|---|---|---|---|---|
| FR | 2882355 | * | 8/2006 | ............. C03C 19/00 |
| GB | 2355660 A | | 5/2001 | |
| JP | 2000274527 | * | 10/2000 | ................. F16J 3/00 |

OTHER PUBLICATIONS

Derwent Publication of Sato's JP2000274527. (Year: 2000).*

*Primary Examiner* — Chee-Chong Lee
(74) *Attorney, Agent, or Firm* — Bryant J. Keller; Kirton McConkie

(57) ABSTRACT

Some implementations of the present invention relate to systems and methods for diffusing scents to a given location by placing a scent reservoir within a vessel including an inner chamber, a vent, and a selectively closable opening. In some cases, the scent reservoir is secured within the vessel while allowing the desired aroma to diffuse into the surrounding area through the vent. In some cases, the inner chamber comprises a wall or layer that is less permeable to the scent than is the vent. Accordingly, in some cases, the inner chamber is configured to direct the scent from the scent reservoir to the vent, which is disposed at an outer surface of the vessel. While the vessel can be any suitable object, in some cases, it is a stuffed animal. Other implementations are also described.

20 Claims, 11 Drawing Sheets

(51) Int. Cl.
*A45D 34/02* (2006.01)
*A63H 3/00* (2006.01)

(56) References Cited

U.S. PATENT DOCUMENTS

| | | | | |
|---|---|---|---|---|
| 5,676,583 | A * | 10/1997 | Wang | A63H 3/00 239/55 |
| 6,089,947 | A * | 7/2000 | Green | A63H 3/003 119/711 |
| 6,299,374 | B1 * | 10/2001 | Naor | B43K 5/00 401/198 |
| 6,422,912 | B1 * | 7/2002 | Summers | A61L 9/12 446/176 |
| 6,520,826 | B2 * | 2/2003 | Spector | A61L 9/12 239/60 |
| 6,699,090 | B1 | 3/2004 | Vick | |
| 9,439,993 | B2 | 9/2016 | Gruenbacher et al. | |
| 2006/0222560 | A1 | 10/2006 | Stanley, III | |
| 2012/0028532 | A1 | 2/2012 | Thompson et al. | |
| 2015/0202340 | A1 | 7/2015 | Warberg Block | |

* cited by examiner

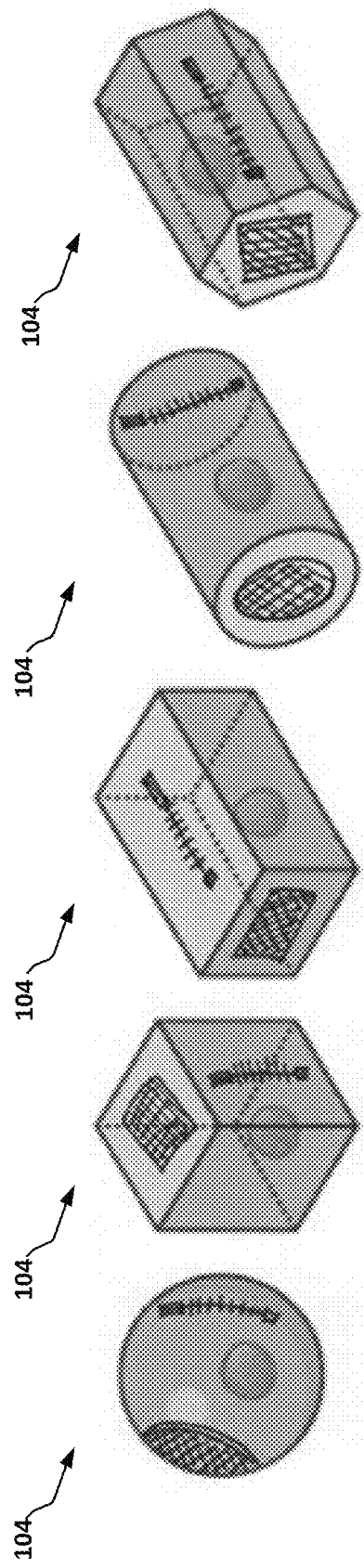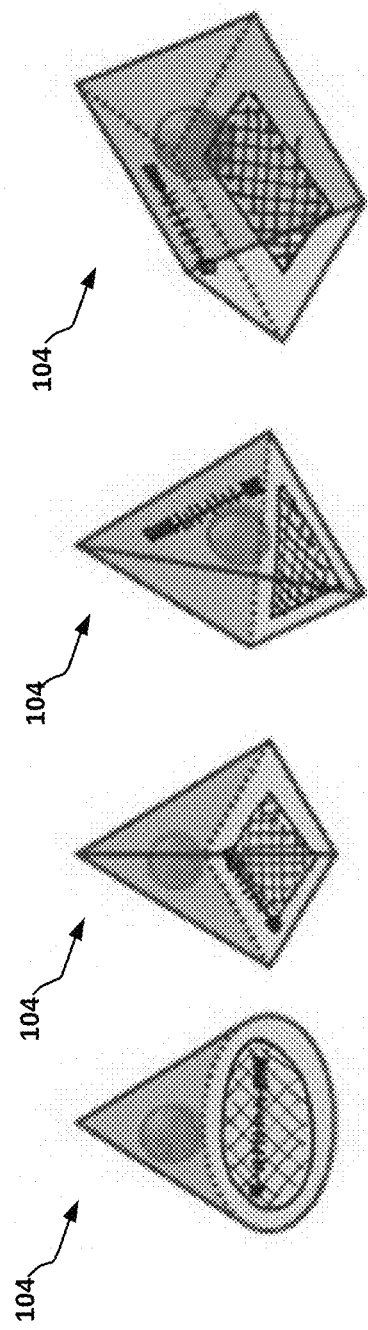

SYSTEMS AND METHODS FOR DIFFUSING ESSENTIAL OILS

RELATED APPLICATIONS

This is a non-provisional utility patent application that claims priority to U.S. Provisional Patent Application Ser. No. 62/580,448, filed on Nov. 2, 2017, and entitled "DEVICE AND METHOD FOR SAFELY DISPENSING SCENTS"; the entire disclosure of which is incorporated herein by reference.

BACKGROUND OF THE INVENTION

Field of the Invention

The present invention relates generally to systems and methods for diffusing scents. In particular, some implementations of the present invention relate to systems and methods for diffusing scents to a given individual, location, or environment by placing a scent reservoir containing a scent source within a vessel including an inner chamber, a vent, and a selectively closable opening. In some such implementations, by enclosing the scent source within the vessel with the vent, a user is protected from direct contact with the scent source, and the scent is able to readily and rapidly diffuse directly from the vent and into the ambient environment.

Background and Related Art

The effective diffusion of a scent or aroma is necessary in a variety of applications. In particular, aromatherapy, deodorizing, and scent based pest control all require the diffusion of a particular scent or aroma beyond a localized scent source. One potential scent source includes essential oils, which require a diffuser or a similar means of dispersing the oils to maximize their efficacy.

Despite the popularity, utility, and widespread use of essential oils and similar scent sources, current diffusers are not necessarily without their shortcomings. By way of example, many diffusers need electricity to help dispense the aroma or scent from the diffusers through the use of sprayers, heat, fans, humidifiers, or a combination of methods that require power or mechanical movement. As a result, these diffusers often need immediate access to an electrical outlet, which often limits where they can be placed.

In some such examples, the diffusers spray a liquid scent source, or a diluted solution containing the liquid scent source, into the air in the form of a mist. While these nebulizers are an effective means of diffusing a liquid, some scent sources include synthetic chemicals that can be harmful or toxic to people, pets, and/or the environment when sprayed directly into the air.

In yet another example, some diffusers require the heating, melting, or burning of scented oils, waxes, gels, or other materials to diffuse a scent. In some cases, this heating, melting, or burning can release airborne toxins. Some of these heat based diffusers, even battery powered diffusers, can present a risk of fire and, in some designs, pose an added hazard of electrical shock. The placement of heat based diffusers is also limited oftentimes because they must be carefully located to ensure they are not near flammable materials as this can increase the risk of fire. Accordingly, current solutions are often limited in their application and/or location as they are very specific in design and purpose. Moreover, the melting or burning of scented products can also release undesirable byproducts into the air. These undesirable byproducts can be harmful to the environment and may be harmful to users that come into contact with the byproducts.

Some manufacturers have attempted to reduce the aforementioned risks and limitations. However, products from such attempts often suffer from reduced effectiveness and muted aromas. To counteract this, strong artificial scents are commonly used. However, these stronger scents can have a negative tradeoff of exposing the user (and others) to more concentrated chemicals and potential allergens.

Thus, while techniques currently exist that are used to diffuse scents, challenges still exist, including those discussed above. Accordingly, it would be an improvement in the art to augment or even replace current techniques with other techniques.

SUMMARY OF THE INVENTION

The present invention relates generally to systems and methods for diffusing scents. In particular, some implementations of the present invention relate to systems and methods for diffusing scents to a given individual, location, or environment by placing a scent reservoir containing a scent source within a vessel including an inner chamber, a vent, and a selectively closable opening. In some such implementations, by enclosing the scent source within a vessel with a vent, the user is protected from direct contact with the scent source, and the scent is able to readily and rapidly diffuse directly from the vent and into the ambient environment—in some cases, without leaving a residual scent in the vessel.

With reference to the scent reservoir, the scent reservoir can comprise virtually any suitable reservoir that can absorb, hold, and/or release a scent. In some implementations, the scent reservoir is configured to contain a scent or combination of scents which can be diffused readily and rapidly from the inner chamber to provide the desired aroma. Some examples of suitable scent reservoirs include, but are not limited to, natural, woven, non-woven, knitted, netting, or technical fabrics or materials; lava rock; bamboo based materials; polymers; ceramics; silica beads; sand; and/or any other suitable materials that can absorb, hold, and/or release a scent. Indeed, in some cases, the scent reservoir comprises wool, cotton, cellulose, and/or any other suitable material that functions as described herein. In this regard, in some particular implementations, the scent reservoir comprises wool that absorbs, holds, and releases aromas from a scent source such as a natural essential oil.

With reference to the vessel, the vessel can comprise any suitable object that is configured to receive the scent reservoir and allow for the diffusion of the scent. In this regard, some implementations of the vessel include an inner chamber, a vent, and a selectively closable opening to allow the scent reservoir to be placed within the vessel, minimize direct physical contact between the user and the scent reservoir, and dispense the scent by natural air dispersion mechanisms. Thus, in at least some implementations, the vessel is easily transportable and can be deployed for use in virtually any chosen location and for virtually any purpose because some implementations utilize natural air dispersion mechanisms and not electrical or mechanical means. In particular, in some non-limiting examples, the vessel can be: carried with the individual for aromatherapy; placed in a drawer, cupboard, and/or other location for pest control; placed into a gym bag, closet, or other location for deodorizing; placed as a decorative and scent diffusing object (e.g., an ornament on a Christmas tree); and/or otherwise be used to diffuse one or more scents.

In this regard, some examples of vessel configurations include, but are not limited to, stuffed animals, air fresheners, bracelets, calming devices, cushions, decorations, (de) odorizers, dolls, figurines, home furnishing items, jewelry, keychains, knick-knacks, novelty items, ornaments, pendants, pillows, rodent/pest control devices, seasonal décor, table-top items, toys, vehicle novelty items, aesthetically pleasing objects, and/or any other desired article for defusing a scent.

The vessel can also comprise a variety of materials to ensure the effective diffusion of a scent through the vent, while minimizing residual scent in the vessel and limiting contact between the user and the scent source. In this regard, some implementations of the vessel comprise natural, woven, non-woven, knitted, netting, synthetic, and/or technical fabrics or materials; leathers; bamboo based materials; polymers; ceramics; rubbers; woods; metals; or any other suitable material or combination of suitable materials. Indeed, in some embodiments, the vessel comprises one or more fabrics, plush fabrics, cloths, terry cloths, felts, plush felts, velboa plush fabrics, long hair plush fabrics, velvets, furs, leathers, microfibers, polyester, rayon, cotton wool, linen, flannel, canvas, silk, lace, faux fur, plush furs, plastics, polymers, metals, ceramics, and/or any other suitable material. In some cases, for instance, an outer surface of the vessel comprises one or more types of cloths or fabrics.

With reference to the inner chamber, some implementations of the inner chamber are designed to receive the scent reservoir. In this regard, an opening may extend through a surface of the vessel to provide access to the inner chamber. In some implementations, the opening is selectively closable.

With reference to the selectively closable opening, some implementations of the selectively closable opening are adjustable between an open position that allows access to the inner chamber, and a closed position that is configured to maintain the scent reservoir within the inner chamber. In some implementations, the selectively closable opening comprises a closing mechanism to provide an open and a closed position. Some examples of closing mechanisms include, but are not limited to, one or more zippers, ties, cords, clips, clamps, crimps, pins, magnets, hooks, loops, hook and loop fasteners, hooks and corresponding eyelets, catches, tabs, slots, buckles, snaps, buttons and/or any other suitable component or components that are configured to allow the vessel to be selectively closed (or sealed) and opened.

With reference to the vent, the inner chamber may extend to a vent positioned in any suitable location, including, without limitation, on a surface of the vessel. In this regard, the vent can be constructed of any suitable material that is substantially permeable and/or breathable to allow the scent to readily and rapidly diffuse from the vessel through the vent. Indeed, in some implementations, the vent is more breathable (or scents can diffuse through the vent more rapidly) that is some material of the vessel that surrounds (or that is otherwise adjacent to) the vent. Some examples of suitable materials for the vent include, but are not limited to, natural, woven, non-woven, knitted, netting, or technical fabrics or materials; polymers; ceramics; metals; and/or any other material that allows a scent to diffuse through it. In some cases, the vent comprises one or more grids, pieces of mesh, screens, pieces of netting, relatively thin pieces of fabric, and/or any other suitable material that allows the scent to diffuse through it relatively rapidly.

Thus, in at least some implementations, the present invention extends to scent diffusing vessels comprising an inner chamber, a vent fluidly connecting the inner chamber to the outside environment, and a selectively closable opening proving selective access to the inner chamber from the outside environment.

By using the described scent diffusing vessel, scent can safely, readily, and rapidly diffuse from a scent reservoir placed within the vessel. In particular, in some implementations that lack the vent, the scent may be trapped, slowed, or muted, with reduced effectivity. In some implementations, the vent allows for the rapid changing of scents because the scent diffuses through the vent and not through the structure of the vessel, which prevents the buildup and retention of earlier scents. Thus, in at least some implementations, the same vessel is used for aromatherapy, deodorizing, pest control, for novelty purposes, and/or for a wide variety of other purposes—reducing the need for multiple scent diffusers. Likewise, in some implementations that lack the selectively closable opening, the scent reservoir may be at risk of falling out of the vessel and rendering the device inoperable, as well as exposing users or others (i.e., children or pets) to direct physical contact with the scent source. As such, in some implementations, the configuration of the vessel is specifically selected to contain the scented object securely while allowing the desired aroma to be diffused and otherwise used to maximum effectiveness.

While the systems and methods of the present invention may be particularly useful for aromatherapy, deodorizing, pest control, and novelty purposes, those skilled in the art will appreciate that the described systems and methods can be used in a variety of different applications and in a variety of different fields of use. For instance, the described systems and methods can be used in any application to readily and rapidly diffuse a scent or aroma directly into a desired environment. Additionally, while some implementations of the described systems and methods are used to diffuse essential oils, the described systems and methods can be used to diffuse any other suitable perfume, fragrance, chemical, natural materials, synthetic materials, and/or other suitable material.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter. As such, this summary is provided to introduce a selection of concepts in a simplified form and is not intended to identify key feature or essential features of the claimed subject matter.

BRIEF DESCRIPTION OF THE DRAWINGS

In order that the manner in which the above-recited and other features and advantages of the present invention are obtained, a more particular description of the invention will be rendered by reference to specific embodiments thereof, which are illustrated in the appended drawings. Understanding that the drawings are not necessarily drawn to scale or in proper proportion, and that the drawings depict only typical embodiments of the present invention and are not, therefore, to be considered as limiting the scope of the invention, the present invention will be described and explained with additional specificity and detail through the use of the accompanying drawings in which:

FIGS. 2A-2I illustrate side perspective (and partially transparent) views of vessel configurations for scent diffusing devices, including a sphere (FIG. 2A), a cube (FIG. 2B), a rectangular prism (FIG. 2C), a cylindrical prism (FIG. 2D), a hexagonal prism (FIG. 2E), a cone (FIG. 2F), a square pyramid (FIG. 2G), a triangular pyramid (FIG. 2H), and/or a triangular prism (FIG. 2I) in accordance with some embodiments;

DETAILED DESCRIPTION OF THE INVENTION

Embodiments of the invention will now be described more fully hereinafter with reference to the accompanying drawings, which are intended to be read in conjunction with the summary, the detailed description, and any preferred and/or particular embodiments, examples, and variations specifically discussed or otherwise disclosed. This invention may, however, be embodied in many different forms and should not be construed as being limited to the embodiments set forth herein; rather, these embodiments are provided by way of illustration only and so that this disclosure will be thorough, complete, and fully convey the full scope of the invention to those skilled in the art.

The present invention relates generally to diffusing scents. In particular, some embodiments of the present invention relate to systems and methods for diffusing scents to a given individual, location, or environment by placing a scent reservoir containing a scent source within a vessel including an inner chamber, a vent, and a selectively closeable opening. In some such embodiments, by enclosing the scent source within the vessel with the vent, the user and others are protected from direct contact with the scent source, and the scent is able to readily and rapidly diffuse directly from the vent and into the vessel's ambient environment without necessarily leaving a residual scent in the vessel.

Figure 1A:
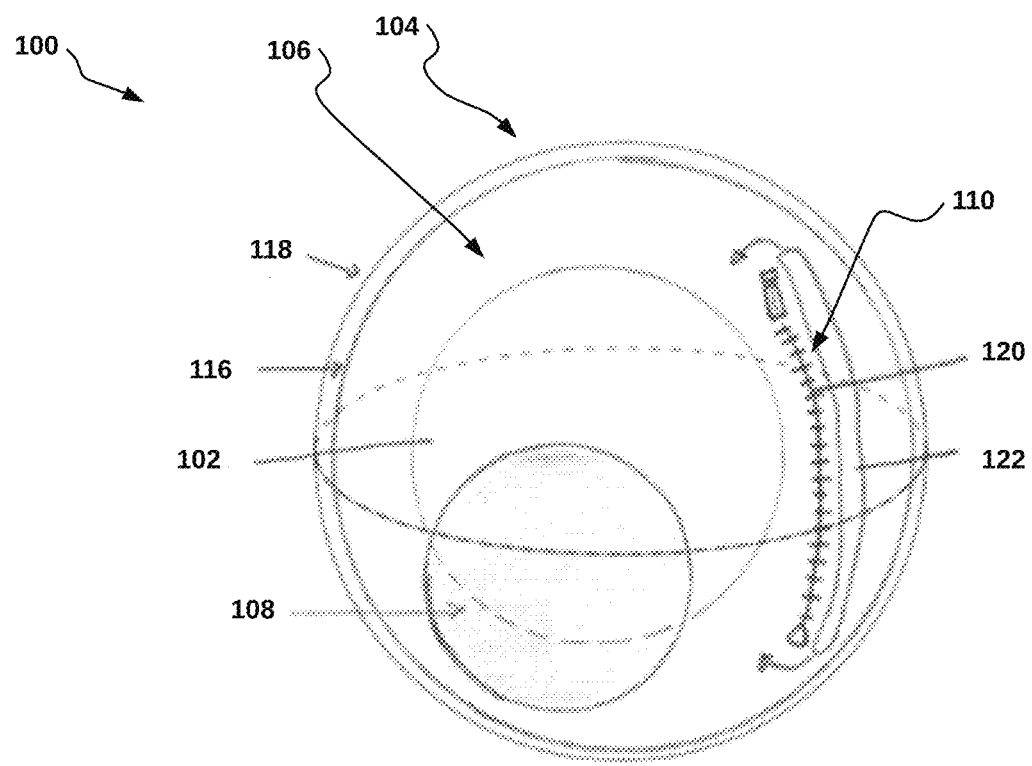
FIG. 1A illustrates a side perspective (and partially transparent) view of a scent diffusing device that includes a scent reservoir that is placed within a spherical vessel that comprises an inner chamber, a vent, and a selectively closable opening in accordance with some embodiments.
Figure 1B:
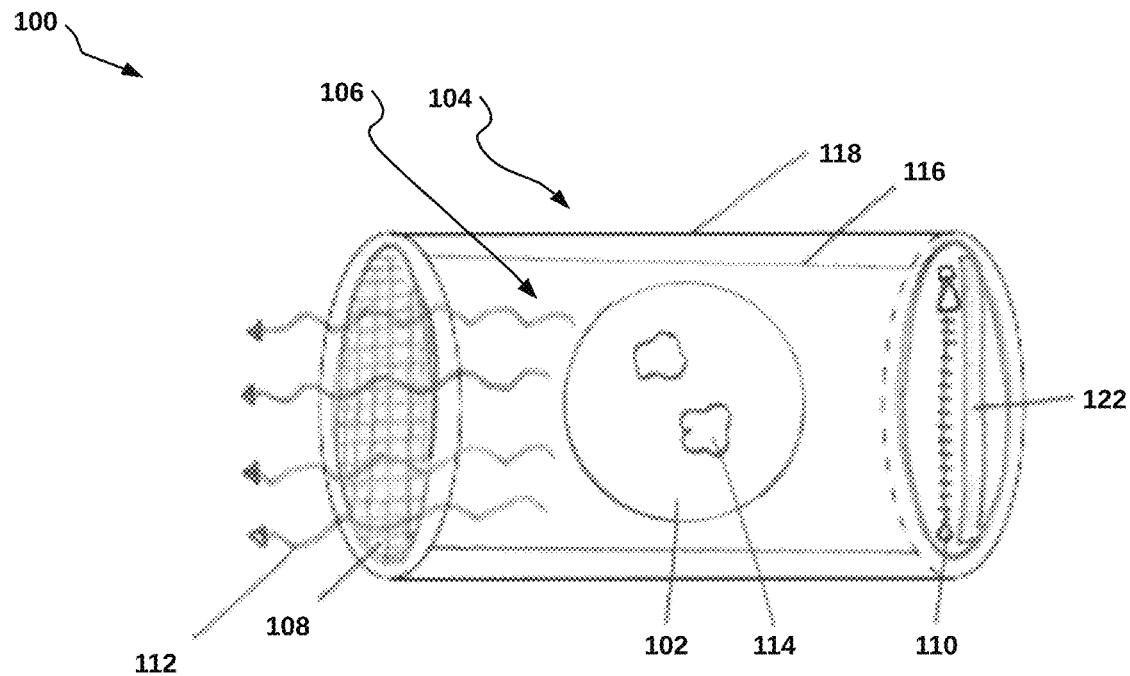
FIG. 1B illustrates a side perspective (and partially transparent) view of the scent diffusing device that includes the scent reservoir that is placed within a cylindrical vessel that comprises the inner chamber, the vent, and the selectively closable opening in accordance with some embodiments.

While the scent diffusing device described herein can include any suitable feature that allow it to diffuse one or more scents (or other materials), FIGS. 1A-1B show that, in some embodiments, the described scent diffusing device 100 comprises a scent reservoir 102 and a vessel 104, wherein the vessel 104 further comprises an inner chamber 106, a vent 108, and a selectively closable opening 110. In the depicted embodiments, the selectively closable opening 110 allows the scent reservoir 102 to be placed within (and/or to be removed from) the inner chamber 106 of the vessel 104. In this regard, once the scent reservoir 102 has been placed within the inner chamber 106, the scent may be diffused by natural air dispersion mechanisms (e.g., as illustrated by the arrows labeled as 112) through the vent 108, while simultaneously preventing the scent reservoir 102 from directly contacting the user and/or absorbing into the vessel 104.

With regard to the scent reservoir 102, the scent reservoir 102 can comprise virtually any suitable object that can absorb, hold, and/or release a scent source 114 (and/or any other suitable diffusible material). In some embodiments, the scent reservoir 102 is configured to contain a scent source 114 or combination of scent sources 114 which can be diffused readily and rapidly from the inner chamber 106 to provide the desired aroma to a given individual, location, or environment. Some examples of such scent reservoirs 102 include, but are not limited to, natural, woven, non-woven, knitted, netting, synthetic, and/or technical fabrics, lava rock, bamboo based materials, polymers, ceramics, silica beads, and/or any other materials that can absorb, hold and/or release a scent. Some non-limiting examples of such include wool, cotton, cellulosic material, nylon, polymers, plastic, polyester, rayon, linen, flannel, silk, lycra, velvet, poly-cotton, yarn, string, batting, and/or any other suitable material. Indeed, as some oils and/or other scents can break down some synthetic materials, in some embodiments, the scent reservoir comprises a natural material, such as wool.

It should also be understood that the scent reservoir 102 may have any suitable size or shape for absorbing, holding, and/or release a scent (or other chemical) and fitting within the inner chamber 106. Indeed, in some embodiments, the scent reservoir 102 has a shape that is partially cuboidal, partially square, partially rectangular, spherical, elliptical, rounded, curved, polygonal, symmetrical, asymmetrical, irregular, and/or any other suitable shape or combination of shapes. Indeed, in some embodiments instead of comprising a swatch of cloth or fabric (e.g., something that can have a substantially two dimensional appearance), the scent reservoir comprises one or more balls, cubes, pyramids, prisms, and/or other suitably shaped object having more of a three dimensional appearance. In some such embodiments, the scent reservoir can further be sized and shaped such that it does not present a choking hazard for children or others.

In some embodiments, the ability to remove the scent reservoir 102 is desired for washing the vessel 104, washing the scent reservoir 102, utilizing disposable scent reservoirs 102, changing scents, replenishing the scent source 114, and/or or using the vessel for multiple applications (i.e. aromatherapy, pest control, deodorizing, and/or any other suitable application) without necessarily leaving residual scents in the vessel. However, in other embodiments, the scent reservoir 102 is not removable. In some such embodiments, the size of the selectively closable opening 110 is optionally minimized because the selectively closable opening 110 need only be large enough to allow the scent source 114 to be applied to the irremovable scent reservoir 102. In accordance with some embodiments, however, FIGS. 1A-B show that the scent reservoir 102 comprises a removable all-natural wool ball (and/or any other material of any other suitable shape and size) that can absorb, hold, and/or release a scent after contacting a scent source 114.

The scent source 114 can comprise any suitable material that is configured to allow a scent and/or another chemical to be diffused from the scent diffusing device 100. In some embodiments, the scent source 114 comprises a liquid, oil, solid, gas, vapor, wax, gel, powder, paste, and/or any other suitable material that is placed in contact with the scent reservoir 102. In this regard, in some particular embodiments, the scent source 114 comprises a mixture of fragrant natural essential oils or aroma compounds, fixatives, and/or solvents that are used to create an agreeable scent that is poured, dabbed, rubbed, dropped, placed on, absorbed in, and/or otherwise applied to the scent reservoir 102.

With regard to the vessel 104, the vessel 104 can comprise any suitable object that is configured to hold one or more scent reservoirs 102 and allow for the diffusion of the scent. In this regard, some embodiments of the vessel 104 comprise an inner chamber 106, a vent 108, and a selectively closable opening 110 that allow the scent reservoir 102 to be placed within the vessel 104, to minimize direct physical contact between the user (and/or others) and the scent reservoir 102, and to readily and rapidly dispense the scent by natural one or more air dispersion mechanisms 112.

With respect to the inner chamber 106, the inner chamber may be designed to receive the scent reservoir 102. In this regard, some embodiments of the inner chamber 106 are formed (e.g., integrally, detachably, and/or otherwise) within the body of the vessel 104. In some embodiments, inner chamber 106 comprises one or more layers 116 that define an interior cavity. In some embodiments, outer layer of the inner chamber comprises a scent permeable material. In some other embodiments, one or more layers 116 of the inner chamber 106 comprise any suitable material that is impermeable or at least substantially impermeable (i.e., does not allow air, fluid, scent, and/or another chemical to pass through it, or that does not allow air, fluid, scent, and/or another chemical to pass through it as quickly as they pass through the vent 108). In some embodiments, a substantially impermeable layer 116 defines the inner chamber 106 and/or serves as a barrier to prevent the scent from diffusing (e.g., as a liquid and/or airborne scent) into the body, stuffing, and/or structure of the vessel 104.

Some examples of suitable layer 116 materials include, but are not limited to, natural, woven, non-woven, knitted, netted, and/or technical fabrics, synthetic and/or semi-synthetic compounds made from polymers, and/or any other suitable material that may prevent the scent from diffusing into the body or structure of the vessel 104 through the layer 116. Indeed, in some embodiments, the layer comprises one or more types of: canvas, nylon, finely woven materials, plastic coated materials, polymer coated materials, polyvinyl chlorides, polyurethanes, silicone elastomer, waxes, fluoropolymers, polytetrafluoroethylenes, plastics, polymers, layers of material having one or more polymer treatments, tightly woven cottons having a one or more polymer coatings, materials that are shown (e.g., by gas chromatography-olfactory (GC-sniffing) and/or otherwise) to have reduced scent transfer, materials noted with reduced transfer of volatile organic compounds, textiles configured for chemical and/or biological protection, carbon fiber materials, materials (e.g., cotton, wool, silk, and/or any other suitable material) that are interwoven with one or more synthetic materials (e.g., one or more polymers, polyesters, and/or any other suitable synthetic materials), materials having one surface coated with one or more polymers and/or polyesters, materials having two sides coated with one or more polymers and/or polyesters, materials impregnated with one or more polymers and/or polyesters, water-resistant microfibers, hydra stretch microfibers, PVC coated nylons, one-sided laminated water resistant jersey, one- or two-sided rubber tarpaulin canvases (and/or other suitable materials), bonded natural fibrous materials, taffetas, taffetas with infused Knott backing, water-resistant polyester twills, performance soft shells woven with fleece backing, nylon Taslans, glasses, and/or any other suitable material that is configured to help cause the scent to diffuse through the vent 108, as opposed to through the layer 116 and into the vessel 104. Indeed, in some embodiments, the layer comprises a waterproof microfiber. Moreover, in some embodiments, the layer 116 of the inner chamber comprises one or more polymers, microfibers, and/or other suitable materials that substantially seal the layer and thereby help ensure that scents are diffused from the vent 108, out of the vessel, and that such scents do not permeate (and/or reduce the amount of such permeation) through the layer and into the vessel 104 (e.g., into stuffing surrounding the inner chamber). Accordingly, in some embodiments, the substantially impermeable layer helps prevent scent residue from building up in the vessel. Thus, in some cases, when one scent source is removed from the vessel 104 another can be added without unduly mixing the two scents.

In some embodiments, the inner chamber 106 optionally extends from one surface 118 of the vessel 104 to one or more other surfaces 118 of the vessel 104. In other embodiments, the inner chamber 106 only extends to one surface 118 of the vessel 104. In accordance with some particular embodiments, FIG. 1B depicts an inner chamber 106 that extends from a first end of the vessel to a second end of the vessel. In still other embodiments, the inner chamber is removable (e.g., for cleaning) and/or replaceable.

The inner chamber 106 can comprise any suitable number of inner compartments, including, without limitation, 1, 2, 3, 4, 5, 6, or more. Indeed, some embodiments, the inner chamber 106 is optionally divided into multiple compartments. In some particular embodiments, the inner chamber 106 is divided into multiple compartments by including baffling that runs through the inner chamber 106. In other embodiments, the inner chamber 106 connects to one or more internal passages that extend through a portion of the interior of the vessel 104.

With regard to the selectively closable opening 110, some embodiments of the selectively closable opening 110 are configured to create one or more openings in one or more surfaces 118 of the vessel 104. In this regard, the selectively closable opening 110 may be adjustable between an open position that allows access to the inner chamber 106, and a closed position that is configured to maintain the scent reservoir 102 within the inner chamber 106 and/or to prevent the scent reservoir 102 from contacting the user inadvertently.

In some embodiments, the selectively closable opening 110 comprises one or more closing mechanisms 120. In this regard, the closing mechanism comprises any suitable mechanism that is configured to selectively close and open. Some examples of suitable closing mechanisms 120 include, but are not limited to, one or more zippers, ties, cords, clips, clamps, crimps, pins, magnets, hooks, loops, hook and loop fasteners, hooks and corresponding eyelets, tabs, slots, buckles, snaps, buttons, and/or any other suitable method for selectively maintaining contact between to items and/or for selectively opening and/or closing (or sealing a portion of) the inner chamber 106. Indeed, in some embodiments, the closing mechanism comprises a zipper. In some embodiments, the vessel 104 optionally includes one or more flaps 122 to cover or conceal the selectively closable opening 110 for aesthetic or safety purposes. Indeed, in some embodiments, the vessel comprises one or more closing mechanisms (e.g., zippers, snaps, etc.) in addition or in place of the flaps.

With regard to the vent 108, the vent 108 may comprise any suitable object or material that is configured to diffuse the scent (and/or any other suitable chemical) from the inner chamber 106 of the vessel 104 to an individual, location, and/or environment outside the vessel 104. In this regard, the vent 108 can be constructed of any suitable material that is substantially permeable and/or breathable to allow the scent to readily and rapidly diffuse from the vessel without the necessity of heat, mechanical, or other powered means. In other words, some embodiments of the vent are more breathable than the substantially impermeable layer 116 and/or the vessel 104 surrounding the inner chamber 106. Some examples of such suitable materials include, but are not limited to, one or more rigid plastics, pliable plastics, types of cotton, types of poly cotton, pieces of wool, types of polyester, bamboo materials, meshes, screens, nettings, relatively thin pieces of cloth or fabric, wool, athletic knits, spandex, non-woven fabrics, molded plastic, perforated plastic, and/or any other suitable material that can keep the scent reservoir 102 within the inner chamber 106 while allowing the scent (or other chemical) to diffuse through the vent more quickly than through the substantially impermeable layer 116. Indeed, in some embodiments the vent comprises a piece of mesh material, a screen, a perforated material, and/or any other suitable material that allows the scent diffusing device to function as described herein.

In some cases, although the vent 108 is more scent permeable than some embodiments of the layer 116, the vent still seals a portion of the inner chamber 106 to prevent the scent reservoir 102 from being able to be removed from the vent while the selectively closable opening 110 is closed. Additionally, in some cases in which the vent is disposed at an outer surface of the vessel 104 such that the vent is at least partially surrounded by material of the outer vessel, the vent comprises a different material that the material that surrounds it. Additionally, in some embodiments, there is little to no batting, feathers, foam, and/or other stuffing disposed between the inner chamber 106 and the vent 108.

As depicted generally in FIGS. 1A-B, in at least some embodiments, the scent diffusing device 100 is easily transportable and can be deployed for use in any chosen location and for any purpose. In particular, in some non-limiting examples, the vessel 104 can be carried (and/or otherwise used) with the individual for aromatherapy; placed in a drawer, cupboard, and/or other location for pest control; placed into a gym bag, closet, car, and/or any other suitable location for deodorizing; and/or in any other suitable location and purpose because some embodiments of the diffusing device are configured to dispense the scent (or other chemical) by natural air dispersion mechanisms 112 and not necessarily by electrical or mechanical mechanisms.

Accordingly, it should be understood that the scent diffusing device 100 may be used in a variety of applications. Indeed, some configurations include, but are not limited to, air fresheners, bracelets, calming devices, cushions, decorations, deodorizers, dolls, figurines, home furnishing items, jewelry, keychains, knick-knacks, novelty items, ornaments, pendants, pillows, rodent/pest control devices, seasonal décor, stuffed animals, table-top items, toys, vehicle novelty items, aesthetically pleasing items, and/or as any other suitable item that is configured to diffuse one or more scents as described herein.

Given the variety of different configurations, it should be understood that the scent diffusing device 100 may comprise a variety of pliable, rigid, resilient, natural, synthetic, and/or other suitable materials based on the desired configuration. Some examples of suitable materials include, but are not limited to, natural, woven, non-woven, knitted, netting, or technical fabric based materials, lava rock, plastics, bamboo based materials, polymers, woods, cellulosic materials, metals, ceramics, any materials listed herein, and/or any other materials for providing aromatherapy to people and animals, for deodorizing or applying a specific odor (odorizing) to a specific location, for the purpose of pest control, for novelty use, and/or for any other suitable use.

Given the variety of different configurations, it should also be understood that the scent diffusing device 100 can comprise a variety sizes and shapes. In this regard, and in accordance with some embodiments, the scent diffusing device 100 is partially cuboidal, partially square, partially rectangular, partially cylindrically, partially spherical, rounded, curved, polygonal, prism shaped, shaped like a toy, shaped as a stuffed animal, shaped as a pillow, symmetrical, asymmetrical, irregular, regular, and/or any other suitable shape or combination of shapes.

With reference to FIGS. 2A-2I, those drawings show that, in some embodiments, the scent diffusing device 100 comprises a vessel 104 in the form of a sphere (FIG. 2A), a cube (FIG. 2B), a rectangular box (FIG. 2C), a cylindrical prism (FIG. 2D), a hexagonal cylinder (FIG. 2E), a cone (FIG. 2F), a square pyramid (FIG. 2G), a triangular pyramid (FIG. 2H), and/or a triangular prism (FIG. 2I).

Figures 3A, 3B, 3C:
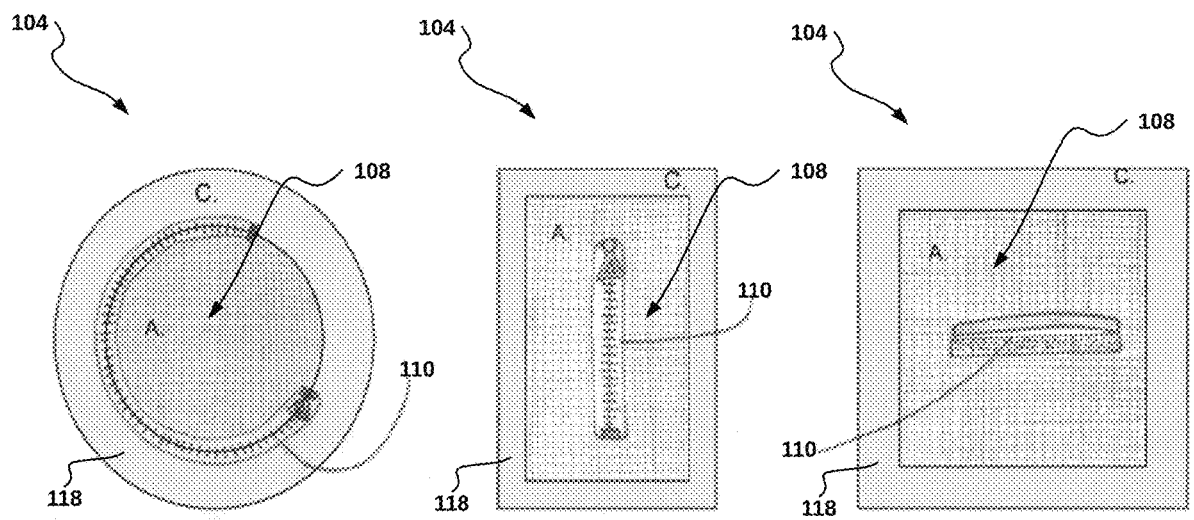
FIGS. 3A-C illustrate a plan view of the scent diffusing device comprising the vent and the selectively closable opening, wherein the vent and selectively closable opening are combined on a single surface (or portion) of the vessel in accordance with some embodiments.

With reference to FIGS. 3A-C, in accordance with some embodiments, the scent diffusing device 100 comprises the vessel 104, wherein the vessel 104 comprises a selectively closable opening 110 and a vent 108. In this regard, where the vessel 104 comprises one or more selectively closable openings 110, each selectively closable opening 110 can be disposed in any suitable location and on any suitable surface of 118 of the vessel 104 to facilitate the effective and efficient placement of the scent reservoir 102 within the vessel 104. Some examples of suitable locations for the selectively closable openings 110 include, without limitation, a top portion, a bottom portion, a side portion (e.g., left side, right side, front side, back side, and/or another side), a middle portion, one or more corners, a belly portion, a head portion, a hand portion, a foot portion, an appendage portion, a back portion, or in any other suitable location (or combinations of locations) on any surface of 118 of the vessel 104.

Likewise, where the vessel 104 comprises 1, 2, 3, 4, 5, 6, 7, or more vents 108, each vent 108 can be disposed in any suitable location and on any surface (or portion) of 118 of the vessel 104 to allow the scent reservoir 102 to readily and rapidly diffuse the scent source 114 by natural air dispersion mechanisms 112. Some examples of suitable locations for the vents 108 include, without limitation, a top portion, a bottom portion, a side portion (e.g., left side, right side, front side, back side, and/or another side), a middle portion, one or more corners, a back portion, a belly portion, a head portion, a hand portion, a foot portion, an appendage portion, or in any other suitable location (or combinations of locations) on any surface of 118 of the vessel 104.

While each selectively closable opening 110 and each vent 108 can be disposed in any suitable location, in some embodiments, the selectively closable opening 110 and the vent 108 are placed on different surfaces 118 of vessel 104 (e.g., as shown in FIGS. 1B, 2A-2I, and 5A-7B). In other embodiments, the selectively closable opening 110 and the vent 108 are placed at different locations on the surface 118 of vessel 104. In yet other embodiments, the selectively closable opening 110 and the vent 108 are placed at the same (or substantially the same) location on the surface 118 of the vessel 104. Indeed, in accordance with at least some embodiments, FIGS. 3A-C depict vessels 104 comprising selectively closable openings 110 and vents 108, where the vents 108 and the selectively closable openings 110 at least partially overlap, or are combined at a single location on a single the surface 118 of the vessel 104.

With further reference to FIGS. 3A-C, where the vessel 104 comprises one or more selectively closable openings 110, each selectively closable opening 110 may have any suitable shape or size to facilitate the effective and efficient placement of the scent reservoir 102 within the vessel 104. Indeed, in some embodiments, each selectively closable opening 110 has a shape that is partially cuboidal, partially square, partially rectangular, rounded, curved, straight, linear, curved, zig-zagged, polygonal, symmetrical, asymmetrical, irregular, and/or any other suitable shape or combination of shapes. By way of non-limiting illustration, FIGS. 3A-C show some embodiments in which the selectively closable openings 110 comprise curved (FIG. 3A) and linear (FIGS. 3A-B) slits that are selectively closable and/or openable. In other embodiments, the selectively closable openings 110 are sized and/or shaped to allow access to the scent reservoir 102 to provide a scent source 114, while preventing the scent reservoir 102 from being unintentionally removed from the vessel 104.

Similarly, where the vessel 104 comprises one or more vents 108, each vent 108 may have any suitable shape or size to readily and rapidly diffuse the scent source 114 by natural air dispersion mechanisms 112. Indeed, in some embodiments, each vent 108 has a shape that is partially: circular, elliptical, star-shaped, moon-shaped, cuboidal, square, shaped like a character, partially rectangular, rounded, curved, polygonal, symmetrical, asymmetrical, irregular, and/or any other suitable shape or combination of shapes. By way of non-limiting illustration, FIGS. 3A-C show some embodiments in which the vents 108 are substantially circular (FIG. 3 A), rectangular (FIG. 3B), and square (FIG. 3C).

Embodiments of the scent diffusing device 100 are used in a variety of applications that require the diffusion of a particular scent, aroma, and/or chemical beyond a localized scent source. Some potential applications include, but are not limited to, decorative items, aromatherapy, deodorizing, and scent based pest control.

FIGS. 4A-D illustrate how, in accordance with some embodiments, the scent diffusing device 100 is configured for decorative purposes to dispense a desired scent and/or other chemical. In particular, FIGS. 4A-D depict an embodiment where the scent diffusing device 100 is configured to resemble a holiday ornament that is hung from a natural or artificial tree and that provides a holiday, festive, and/or other suitable scent or aroma. In this regard, the scent diffusing device 100 can be used in conjunction with a scent source 114 (not depicted) comprising pine, cinnamon, wassail, and/or any other suitable holiday, festive, and/or other suitable scent or aroma.

Figure 4A:
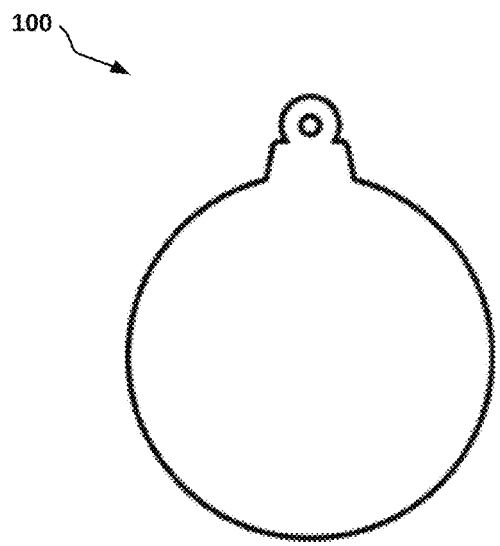
FIG. 4A illustrates a front side view of a scent diffusing device that is configured as a Christmas tree ornament in accordance with some embodiments.
Figure 4B:
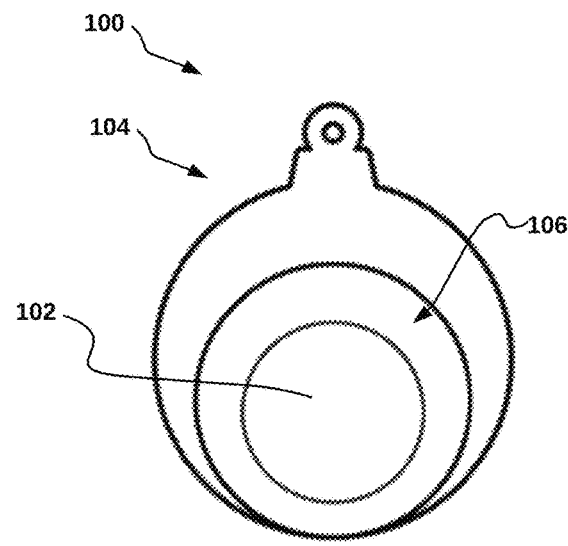
FIG. 4B illustrates a cutaway side view of the scent diffusing device that is configured as a Christmas tree ornament, where the scent diffusing device comprises an inner chamber and a scent reservoir that is placed within the inner chamber in accordance with some embodiments.

As depicted in FIG. 4B, in some embodiments, the scent diffusing device 100 comprises a vessel 104, an inner chamber 106 within the vessel 104, and a scent reservoir 102, wherein the inner chamber 106 is sized and shaped to receive and retain the scent reservoir 102. FIG. 4B depicts one particular embodiment, where the scent reservoir 102 comprises a ball comprising wool and/or any other suitable material and that is placed within the inner chamber 106.

Figure 4C:
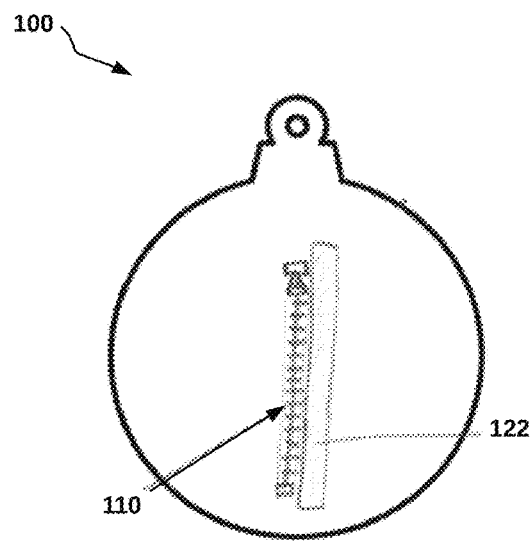
FIG. 4C illustrates a back side view of the scent diffusing device that is configured as a Christmas tree ornament, where the scent diffusing device includes the selectively closeable opening on the back surface of the vessel in accordance with some embodiments.
Figure 4D:
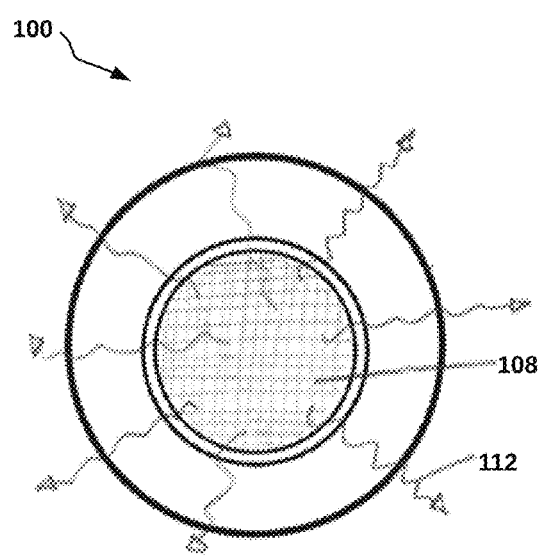
FIG. 4D illustrates a bottom side view of the scent diffusing device that is configured as a Christmas tree ornament, where the scent diffusing device includes a vent on a bottom surface of the vessel that is configured to diffuse a scent in accordance with some embodiments.

In accordance with at least some embodiments, FIGS. 4C-D depict a selectively closable opening 110 on the back of the vessel 104 and a vent 108 on the bottom of the vessel 104. In at least some embodiments, once the scent source 114 (not depicted) has been absorbed by and/or otherwise applied to the scent reservoir 102 (FIG. 4B) and placed within the inner chamber (FIG. 4B) through the selectively closable opening 110 (FIG. 4C), the scent is diffused by natural air dispersion mechanisms 112 (FIG. 4D) through the vent 108 (FIG. 4D).

The vessel 104 can comprise any internal material, including, without limitation, one or more types of batting, foam, memory foam, Dacron, shredded materials, cotton, wool, polyester, and/or other types of stuffing. Thus, in some embodiments, the vessel comprises any suitable stuffed object (e.g., a stuffed animal, an ornament, and/or any other suitable object).

Figures 5A, 5B, 5C:
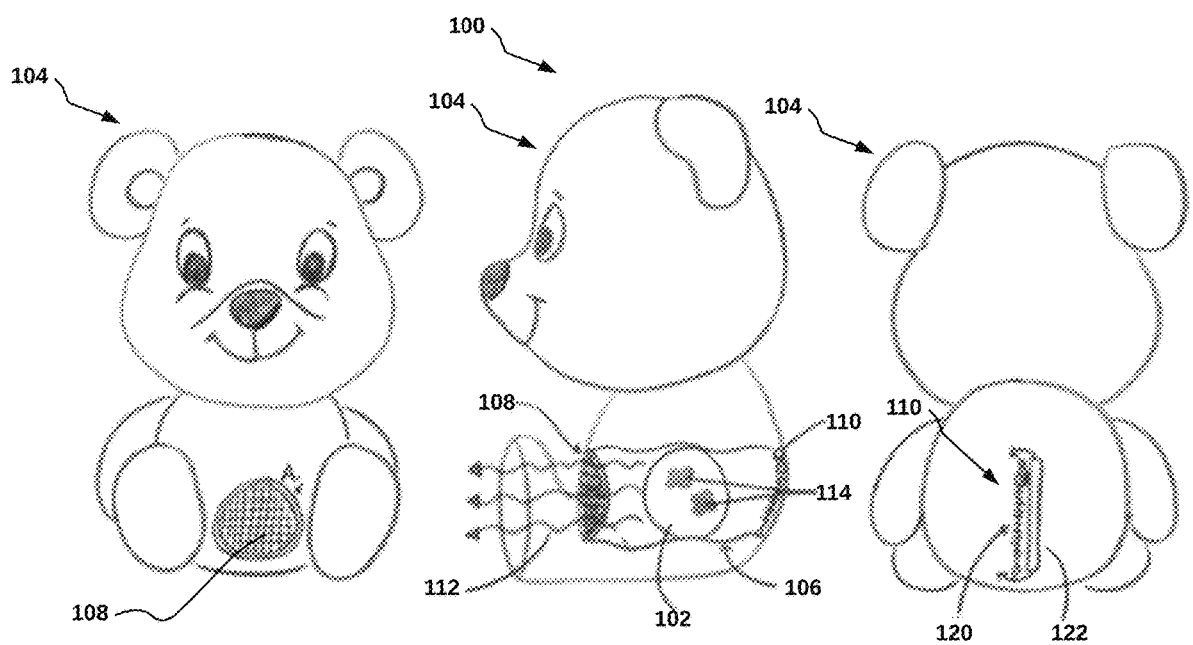
FIG. 5A illustrates a front side view of a scent diffusing device comprising a stuffed animal, where the scent diffusing device includes the vent on a front surface of the vessel in accordance with some embodiments.
FIG. 5B illustrates a side, partially cutaway, view of the scent diffusing device that is configured as a teddy bear, where the scent diffusing device includes the inner chamber and the scent reservoir that is placed within the inner chamber in accordance with some embodiments.
FIG. 5C illustrates a back side view of the scent diffusing device that is configured as a teddy bear, where the scent diffusing device includes selectively the closeable opening on a back surface (or portion) of the vessel in accordance with some embodiments.
Figure 6A:
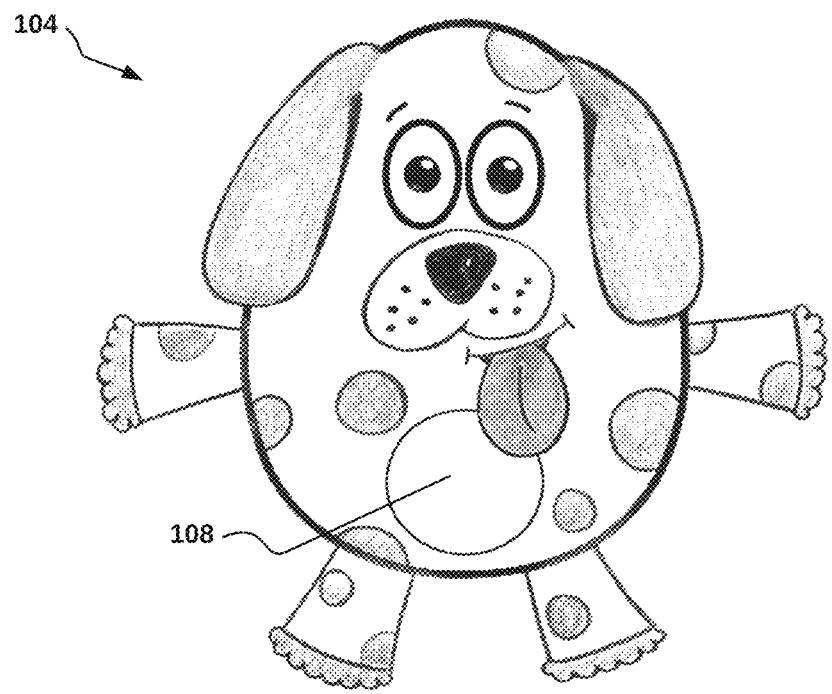
FIGS. 6A-6B each illustrate a different view of the scent diffusing device that is configured as a stuffed animal resembling a dog, where the scent diffusing device includes the vent on the front surface of the vessel and the selectively closable opening on the back surface of the vessel in accordance with some embodiments.
Figure 6B:
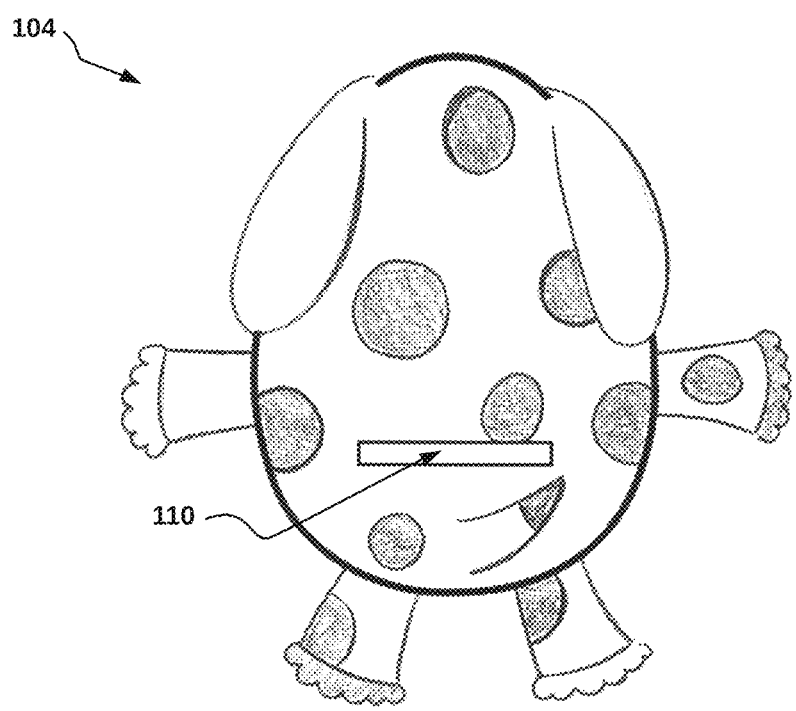
Figure 7A:
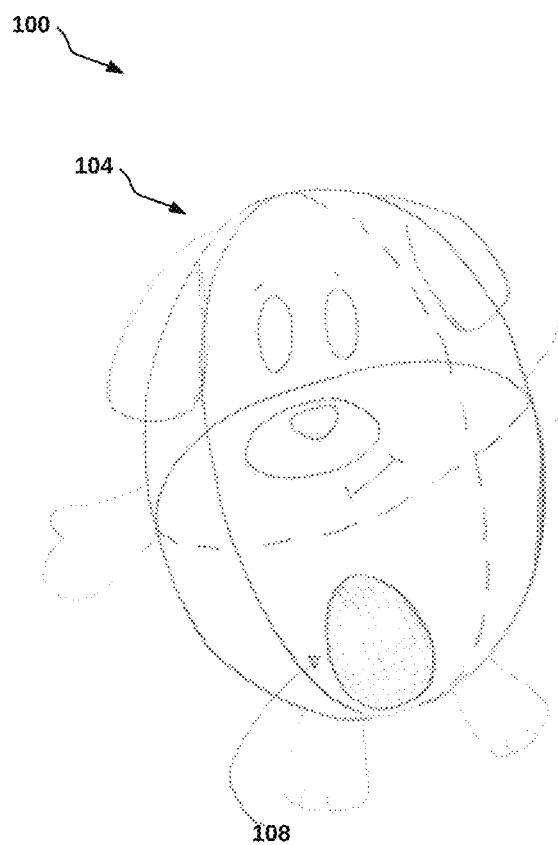
FIGS. 7A-7B illustrate the scent diffusing device that is configured as a stuffed animal resembling a dog where the scent diffusing device includes the inner chamber and the scent reservoir that is placed within the inner chamber in accordance with some embodiments.
Figure 7B:
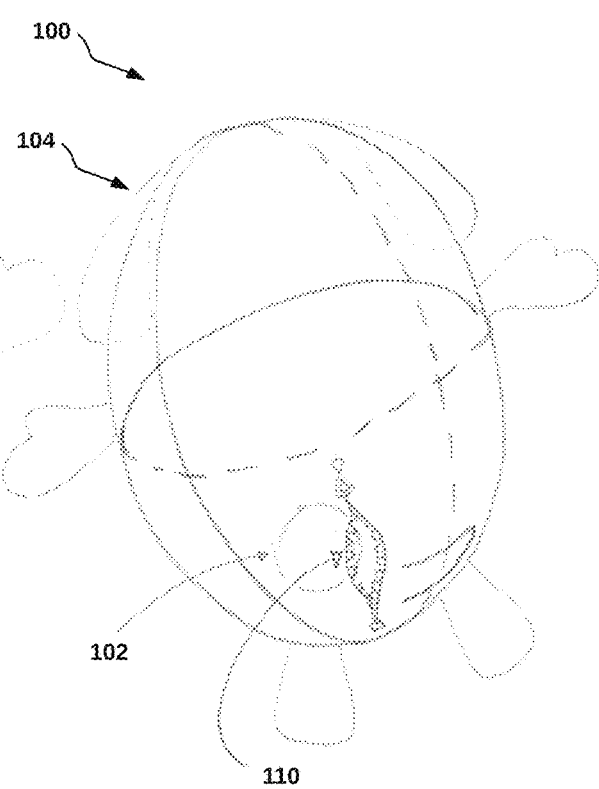

By way of non-limiting illustration, FIGS. 5A-5C illustrate how, in accordance with some embodiments, the scent diffusing device 100 is configured to resemble a stuffed animal (e.g., a teddy bear and/or any other suitable stuffed object), which is used for aromatherapy or any other suitable purpose for a child or other person. In this regard, the scent diffusing device 100 can be used in conjunction with a scent source 114 (FIG. 5B) comprising lavender, peppermint, eucalyptus, lemon, tea tree, mint, or any other suitable scent or combination of scents (e.g., scents that are selected to balance, harmonize, and/or promote the health of body, mind, and/or spirit).

In accordance with at least some embodiments, FIGS. 5A-C depict a selectively closable opening 110 on the back of the vessel 104 configured to resemble a stuffed animal and a vent 108 on the front of the vessel 104 configured to resemble the stuffed animal. In at least some embodiments, once the scent source 114 (FIG. 5B) has been absorbed by and/or otherwise applied to the scent reservoir 102 (FIG. 5B) and placed within the inner chamber 106 (FIG. 4B) through the selectively closable opening 110 (FIG. 5C), the scent is readily and rapidly diffused (FIG. 5B) through the vent 108 (FIG. 5B-5C). In some embodiments, the closing mechanism 120 is optionally covered by one or more flaps 122 to hide or otherwise cover the closing mechanism 120.

While FIGS. 5A-5C depict a scent diffusing device 100 that is configured to resemble a plush, teddy bear, it should be understood that the scent diffusing device 100 can be configured to resemble a variety of stuffed animals and/or other objects. In this regard, the scent diffusing device 100 can allow those who may require aromatherapy, especially children, to receive such therapy without the negative stigma often associated with such treatment because the innocuous shape of a stuffed animal does not necessarily call attention to the purpose of the device.

Figure 8:
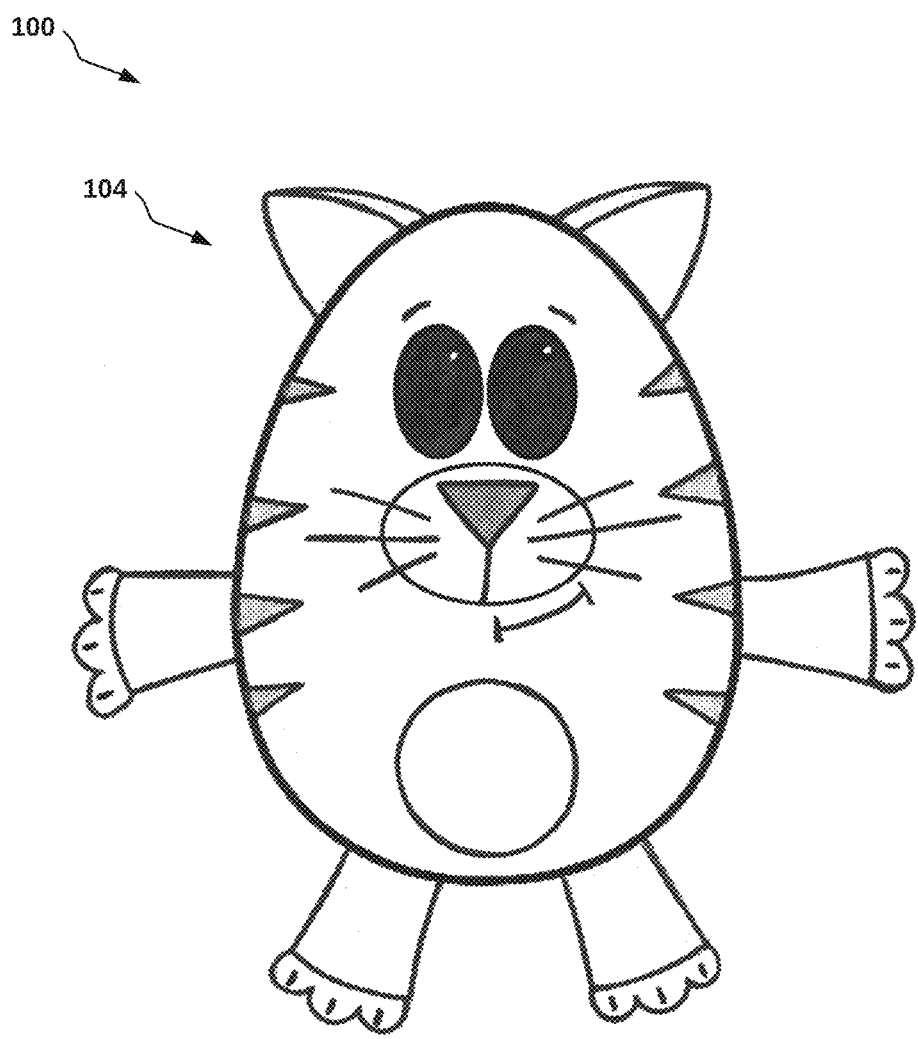
FIG. 8 illustrates a front side view of the scent diffusing device that is configured as a stuffed animal resembling a cat in accordance with some embodiments.

With respect to FIGS. 6A-B and 7A-B, in some embodiments, the scent diffusing device 100 is configured as a stuffed animal that resembles a dog (and/or any other suitable creature). In this regard, the scent diffusing device 100 can effectively diffuse scent, while being easily transported and placed in a variety of locations because it is untethered by electrical connection. Moreover, FIG. 8 depicts one particular embodiment where the scent diffusing device 100 is configured to resemble a cat.

Figure 9:
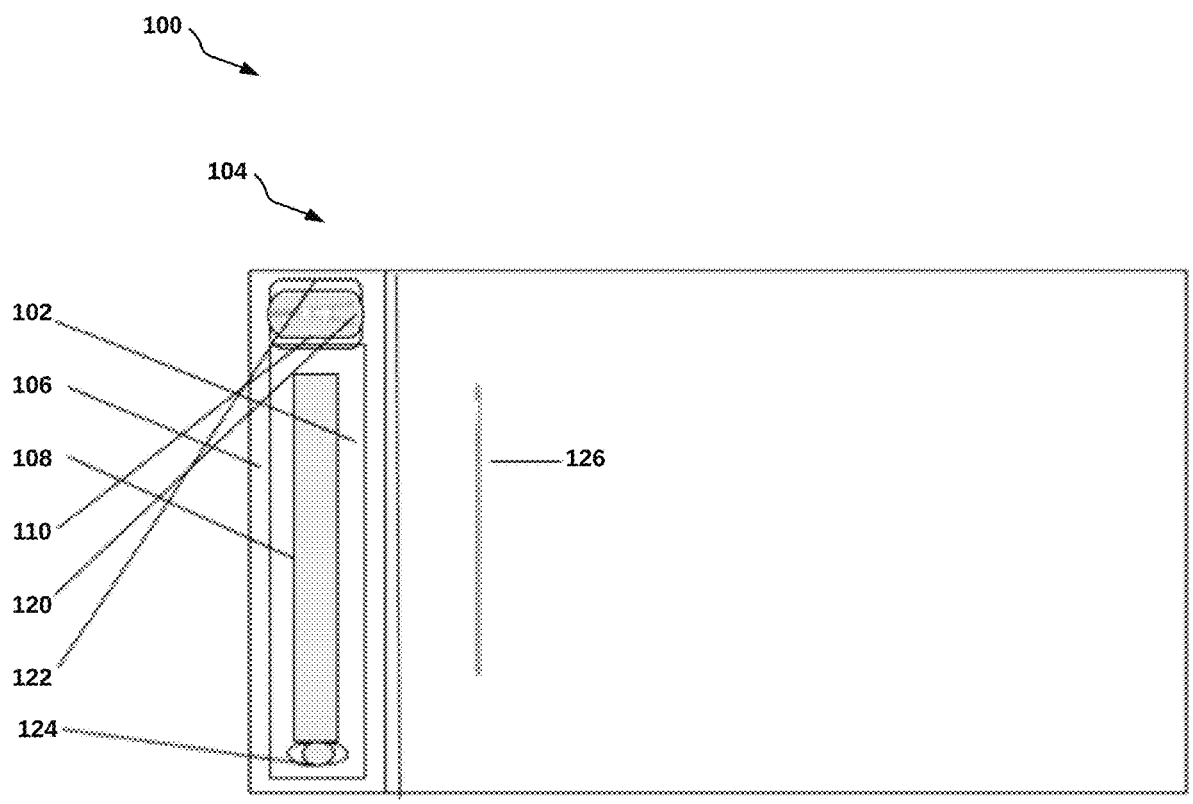
FIG. 9 illustrates a top view of a scent diffusing device that is configured as a pillow (or a pillow case) in accordance with some embodiments.

FIG. 9 illustrates how, in accordance with some embodiments, the scent diffusing device 100 is configured to resemble a pillow (and/or pillowcase) that may be used for aromatherapy (and/or any other suitable reason) for adults and children. In this regard, FIG. 9 depicts a particular embodiment, where the scent diffusing device 100 comprises a vessel 104 resembling a pillow, a scent reservoir 102, a vent 108, a selectively closable opening 110, a closing mechanism 120, a flap 122 to cover the selectively closable opening 110, a closing mechanism 120, an access opening 124 to allow for the placement of the internal vessel materials, and a hook (and/or any other suitable implement) 126 to easily feed the internal vessel materials (e.g., the internal compartment) into the vessel 104. In accordance with some particular embodiments, the scent reservoir 102 optionally comprises a wood or natural bamboo strip and/or any other suitable reservoir. In this regard, such a reservoir can be irremovable or selectively removable. In accordance with some particular embodiments, the vent 108 comprises a large elongated mesh (and/or any other suitable) venting material (e.g., a material that is configured to allow a scent to flow through it more readily then it would through substantially impermeable layer and/or another portion of the vessel). In accordance with some particular embodiments, the closing mechanism 120 comprises a zipper and/or any other suitable closing mechanism. In accordance with some embodiments, the internal vessel materials (e.g., the padding of the pillow) comprise one or more gels, polyester, feathers, latex, visco-elastic materials, and/or any other similar material. That said, the elements of such a vessel can be rearranged in any suitable manner.

Figure 10:
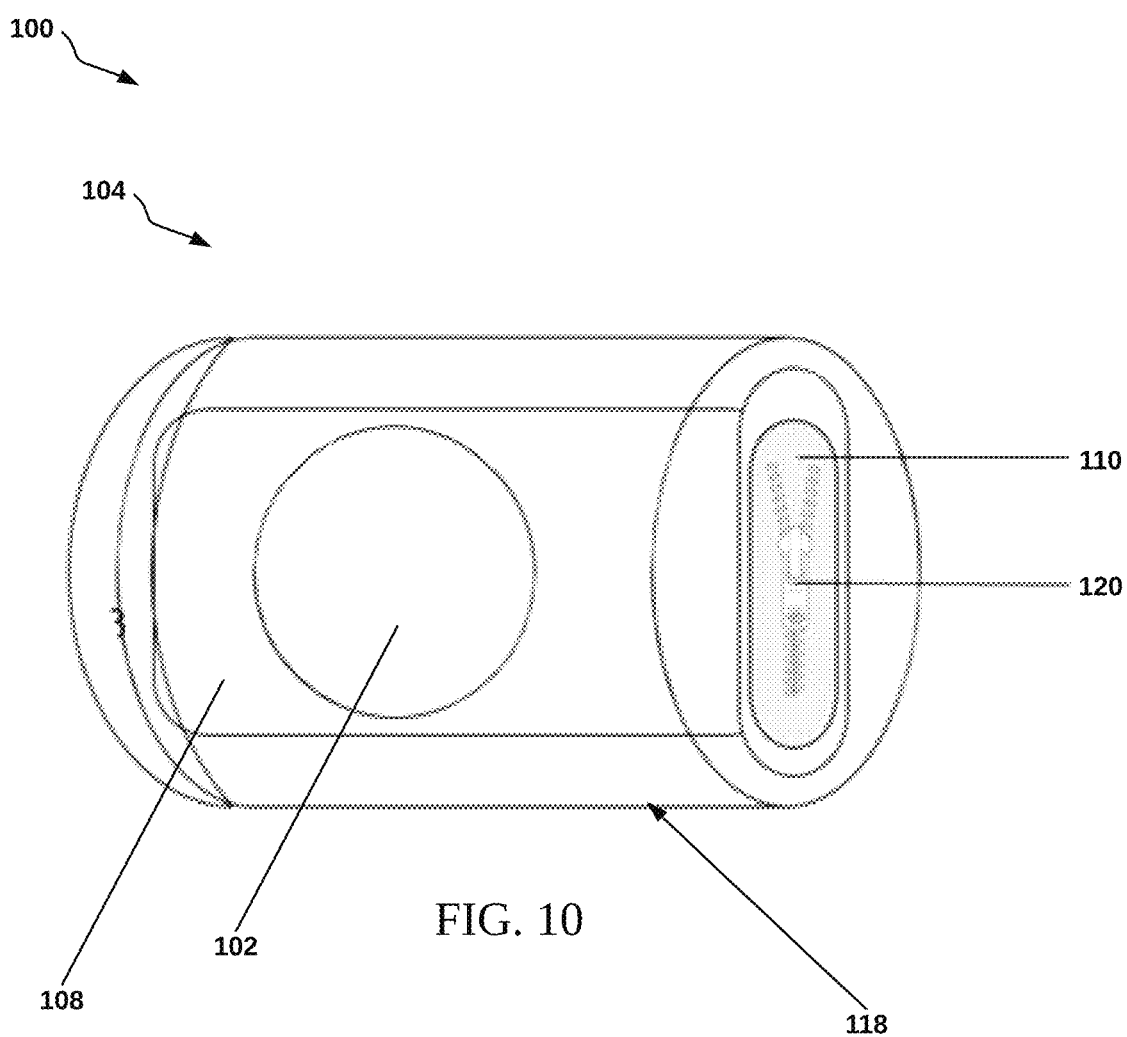
FIG. 10 illustrates a top perspective (partially transparent) view of the scent diffusing device that is configured as an essential oil (or other scent) deodorizer in accordance with some embodiments.

FIG. 10 illustrates how, in accordance with some embodiments, the scent diffusing device 100 is configured as a deodorizer. In this regard, the scent diffusing device 100 may be used in conjunction with a scent source 114 (not depicted) comprising lavender, chamomile, ylang ylang, clary sage, lemon, orange, bergamot, peppermint, geranium, cypress, cedar wood, white fur, eucalyptus, white fir, or any other suitable scent or combination of suitable scents that are selected as an air freshener or deodorizer.

In accordance with at least some embodiments, FIG. 10 depicts a selectively closable opening 110 on a first side of the vessel 104 and a vent 108 on second side of the vessel 104. In at least some embodiments, once the scent source 114 has been absorbed by and/or otherwise applied to the scent reservoir 102 and placed within the inner chamber through the selectively closable opening 110, the scent is diffused through the vent 108. In accordance with some particular embodiments, the scent reservoir 102 comprises a wool ball (and/or any other suitable shaped material). In accordance with some particular embodiments, the vent 108 comprises mesh (and/or any other suitable) venting material. In accordance with some particular embodiments, the closing mechanism 120 comprises a zipper (and/or another suitable closure). In accordance with some particular embodiments, the vessel 104 comprises a hard outer shell, a ridged surface 118, and/or any other suitable material.

Figure 11:
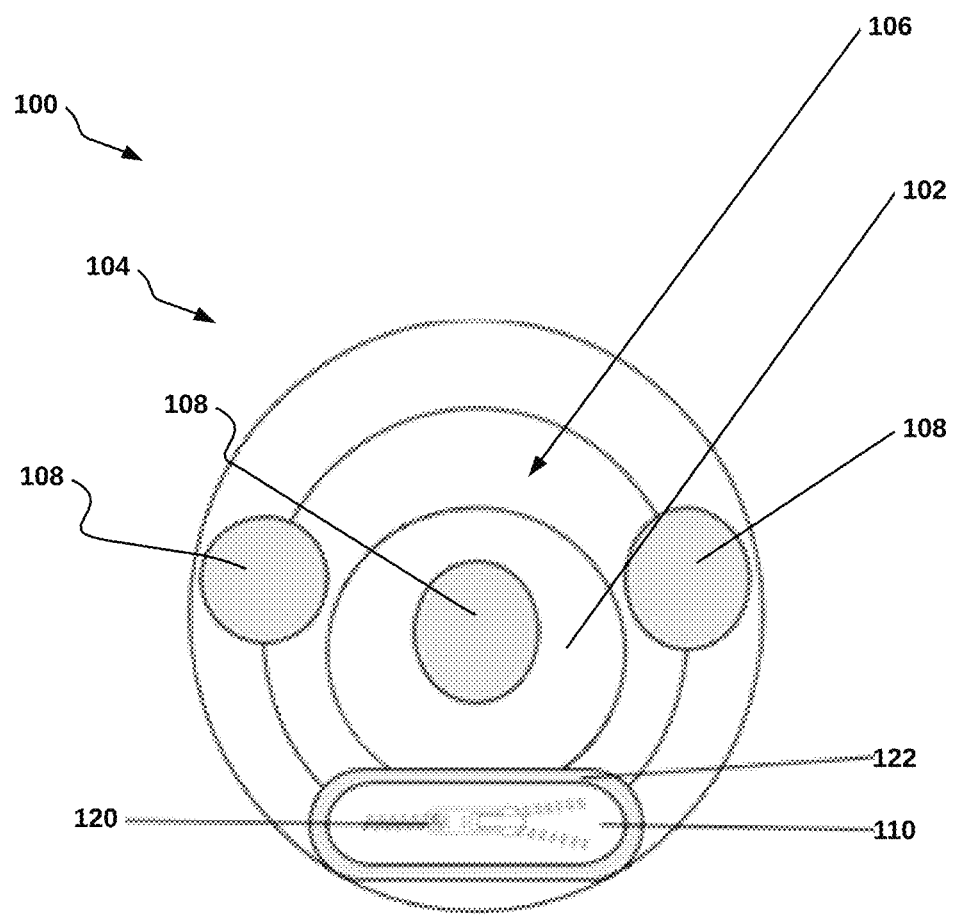
FIG. 11 illustrates a top perspective view of the scent diffusing device that is configured for pest control, where the scent diffusing device includes multiple vents in accordance with some embodiments.

FIG. 11 illustrates how, in accordance with some embodiments, the scent diffusing device 100 is configured for pest control. In this regard, the scent diffusing device 100 may be used in conjunction with a scent source 114 comprising cedar wood, citronella, eucalyptus, hyssop, lavender, lemongrass, patchouli, peppermint, sage, spearmint, thyme, and/or any other suitable scent or combination of scents (or chemicals) that are selected to target, repel, kill, and/or otherwise prevent pests.

In accordance with at least some embodiments, FIG. 11 depicts a selectively closable opening 110 and any suitable number of vents 108 (e.g., three) that are disposed on a top surface of the vessel 104. In at least some embodiments, once the reservoir 102 has been placed within the inner chamber 106 through the selectively closable opening 110, the scent is diffused through the three vents 108. In accordance with some particular embodiments, the multiple vents 108 provide multidirectional aroma disbursement.

In addition to the aforementioned features, the described scent diffusing device can comprise any other suitable feature, including, without limitation, one or more fans, heaters, misters, nebulizers, batteries, switches, lights, buttons, decorative objects, haptic vibrators, speakers, and/or any other suitable components.

Accordingly, various embodiments of the invention have many different features, variations and multiple different embodiments. Moreover, the invention has been described in this application at times in terms of specific embodiments for illustrative purposes and without the intent to limit or suggest that the invention conceived is only one particular embodiment. It is to be understood that the invention is not limited to any single specific embodiments or enumerated variations. Many modifications, variations, and other embodiments of the invention will come to mind of those skilled in the art to which this invention pertains, and which are intended to be and are covered by both this disclosure.

It is indeed intended that the scope of the invention should be determined by proper interpretation and construction of the disclosure, including equivalents, as understood by those of skill in the art relying upon the complete disclosure at the time of filing.

As described herein, the scent diffusing device 100 may offer several advantages over certain prior art scent diffusers. In some embodiments, the scent diffusing device provides a safe method of releasing scent without muting or requiring additional materials or methods to boost aroma diffusion. In other embodiments, the scent diffusing device does not require any electricity or mechanical help to diffuse the aroma, scent, and/or other chemical into the environment which vastly increases versatility and mobility. In yet other embodiments, the scent diffusing device does not release, mist, or spray potentially dangerous chemicals into the air, but relies on Brownian motion and/or any other suitable principles of air flow for effective release and diffusion of scents and natural oils. In this regard, the scent diffusing device may avoid producing and release toxic or cancer-causing matter. In other embodiments, the scent diffusing device uses no heating mechanism or electricity. In this regard, the scent diffusing device may eliminate or minimize a risk of fire or a potential for electric shock. In yet other embodiments, the scent diffusing device allows the user to customize the diffused scent(s) with safe and natural solids, liquids, vapors, or gases with minimal direct handling of the chosen scent by encasing the scent source in the vessel. In other embodiments, the scent diffusing device alleviates the need for multiple devices by allowing the user to change or combine scents at any time as well as relocate the device as desired. In yet other embodiments, the proposed invention, when used properly, dramatically reduces and usually eliminates the potential for harm or injury to the user, pet, or environment by utilizing a scent source comprising natural oils and scents.

The present invention may be embodied in other specific forms without departing from its spirit or essential characteristics. The described embodiments, examples, and illustrations are to be considered in all respects only as illustrative and not restrictive. The scope of the invention is, therefore, indicated by the appended claims rather than by the foregoing description. All changes that come within the meaning and range of equivalency of the claims are to be embraced within their scope. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., front back, on top of, below, above, top, bottom, side, up, down, under, over, upper, lower, lateral, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

What is claimed is:

1. A scent diffusing device comprising:
a scent reservoir; and
a vessel, wherein the vessel defines an internal compartment that comprises:
an inner chamber that extends through, is disposed in, and is separated from, the internal compartment of the vessel, with the inner chamber comprising:
a flexible wall that defines a portion of the inner chamber, that is disposed within the internal compartment of the vessel, that separates the inner chamber from the internal compartment, and that is configured to help prevent a scent from the scent reservoir from diffusing through the flexible wall into the internal compartment of the vessel; and
a scent-permeable vent that is coupled to, and that is more scent permeable than is, the flexible wall that separates the inner chamber from the internal compartment, such that the inner chamber is configured to channel the scent through the scent-permeable vent,
wherein the scent reservoir is selectively received within the inner chamber.

2. The scent diffusing device of claim 1, wherein the inner chamber further comprises a selectively closable opening, wherein the selectively closable opening is configured to be selectively closed and opened, wherein the selectively closable opening is sized and shaped to allow the scent reservoir to pass through the selectively closable opening when the selectively closable opening is opened and to prevent the scent reservoir from passing through the selectively closable opening when the selectively closable opening is closed, and wherein the scent-permeable vent is disposed at a first external surface of the vessel and the selectively closable opening is disposed at a second external surface of the vessel.

3. The scent diffusing device of claim 1, wherein the flexible wall that separates the inner chamber from the internal compartment of the vessel comprises at least one of: (i) a woven barrier, (ii) a cloth barrier, (iii) a fabric barrier, and (iv) a knitted barrier that is configured to prevent the scent from diffusing into the vessel through the flexible wall, and wherein the scent-permeable vent comprises at least one of: (a) a woven material, (b) a cloth material, (c) a fabric material, (d) a screen, (e) a mesh, and (f) a piece of netting that is more scent-permeable than is the flexible wall.

4. The scent diffusing device of claim 1, wherein the scent reservoir comprises a first essential oil, and wherein the scent reservoir comprises a washable material that is configured to be washed such that the first essential oil is removed from the scent reservoir and such that a second essential oil can be added to the scent reservoir.

5. The scent diffusing device of claim 1, wherein the scent-permeable vent, which is coupled to the flexible wall that defines the portion of inner chamber and that is disposed in the internal comportment, is flush with an external surface of the vessel.

6. The scent diffusing device of claim 1, wherein the scent reservoir comprises wool.

7. The scent diffusing device of claim 6, wherein the scent reservoir comprises a ball.

8. The scent diffusing device of claim 1, wherein the flexible wall that defines the portion of the inner chamber and that separates the inner chamber from the internal compartment comprises a material that is configured to prevent the scent of the scent reservoir from diffusing through the flexible wall and into the internal compartment of the vessel, and wherein the flexible wall comprises at least one of: (i) a woven material, (ii) a cloth, and (iii) a fabric.

9. A scent diffusing device comprising:
a scent reservoir configured to receive a scent source; and
a vessel that defines an internal compartment and that comprises:
an inner chamber comprising:
a flexible wall that defines a portion of the inner chamber and that extends through and is disposed within the internal compartment of the vessel;
a flexible, scent-permeable vent that is coupled to the flexible wall and that is more scent permeable than is the flexible wall so as to prevent scent from the scent source from diffusing into the internal compartment while allowing the scent from the scent source to diffuse out of the inner chamber through the flexible, scent-permeable vent; and
a selectively closable opening that is configured to selectively close to capture the scent reservoir within the inner chamber and to selectively open to release the scent reservoir from the inner chamber,
wherein the inner chamber extends through and is disposed within the internal compartment of the vessel and is separated from the internal compartment by the flexible wall, with the flexible, scent-permeable vent being disposed at a first external surface of the vessel and such that the selectively closable opening is disposed at a second external surface of the vessel.

10. The scent diffusing device of claim 9, wherein the first external surface comprises at least one of a front surface and a back surface of the vessel, and wherein the second external surface comprises the other of the at least one of the front surface and the back surface of the vessel.

11. The scent diffusing device of claim 9, wherein the flexible, scent-permeable vent comprises a material that is integrally coupled to both the first external surface of the vessel and to an end of the flexible wall, and wherein the material is configured to extend across an opening at the end of the flexible wall and to prevent the scent reservoir from passing through the material.

12. The scent diffusing device of claim 9, further comprising a flexible flap that is configured to selectively cover a portion of the selectively closable opening, wherein the flexible flap is disposed at the second external surface, external to the internal compartment.

13. The scent diffusing device of claim 9, wherein the vessel comprises at least one of a pillow, a pillowcase, and a gym bag.

14. A scent diffusing device comprising:
a vessel comprising an inner cavity that comprises a stuffing, the vessel comprising a first external surface and a second external surface, with a portion of the second external surface being disposed opposite to a portion of the first external surface, and with a portion of the stuffing being disposed between the first external surface and the second external surface;
an inner chamber that extends through and is disposed in the inner cavity of the vessel so as to extend between the first external surface and the second external surface, the inner chamber comprising:
a flexible wall that defines a portion of the inner chamber, that separates the inner chamber from the inner cavity, and that is disposed within the inner cavity of the vessel so as to extend between the first external surface and the second external surface;
a flexible, scent-permeable vent that is disposed at an end portion of, and is coupled to, the flexible wall and that is disposed at the first external surface of the vessel, with the flexible, scent-permeable vent being more scent-permeable than is the flexible wall such that the flexible wall helps prevent a first scent in the inner chamber from diffusing into the inner cavity and to allow the first scent in the inner chamber to diffuse out of the inner chamber through the flexible, scent-permeable vent; and
a selectively closable opening that is configured to selectively close to capture a scent reservoir within the inner chamber and to selectively open to release the scent reservoir from the inner chamber, wherein the selectively closable opening is disposed at the second external surface of the vessel.

15. The scent diffusing device of claim 14, further comprising the scent reservoir, with the scent reservoir comprising a material that is disposed within the inner chamber, wherein the scent reservoir comprises a first scent source that provides the first scent, wherein the scent reservoir comprises a washable material that is configured to be washed to remove the first scent source, and wherein the scent reservoir is configured to receive a second scent source that has a different scent than the first scent.

16. The scent diffusing device of claim 14, wherein an entire perimeter of the flexible, scent-permeable vent is integrally coupled to a perimeter of the flexible wall.

17. The scent diffusing device of claim 14, wherein the flexible, scent-permeable vent is integrally coupled to a perimeter of the flexible wall.

18. The scent diffusing device of claim 14, wherein the flexible wall comprises a scent impermeable material that is configured to help prevent a scent applied to the scent reservoir from penetrating through the flexible wall and diffusing into inner cavity of the vessel.

19. The scent diffusing device of claim 18, wherein the scent impermeable material comprises an organic material selected from at least one of: (i) a woven material, (ii) a cloth, and (iii) a fabric.

20. The scent diffusing device of claim 19, wherein the vessel comprises a stuffed figure, wherein the first external surface is disposed at a front side of the stuffed figure, and wherein the second external surface is disposed at a back side of the stuffed figure.

* * * * *